United States Patent [19]

Brisset et al.

[11] Patent Number: 4,497,743

[45] Date of Patent: Feb. 5, 1985

[54] ORGANOSOLUBLE SALTS OF MANGANESE, PROCESS OF PREPARATION OF SAME

[76] Inventors: Guy C. S. Brisset, 16 rue des Sittelles, St. Just 27200 Vernon; Michel C. Mas, 7 rue J. F. Millet, 78200 Mantes La Ville, both of France

[21] Appl. No.: 278,304

[22] Filed: Jun. 29, 1981

[51] Int. Cl.$^3$ .............................................. C07F 13/00
[52] U.S. Cl. ................................................ 260/429 R
[58] Field of Search ................... 260/429 R, 414, 441; 44/66

[56] References Cited

U.S. PATENT DOCUMENTS

| | | | |
|---|---|---|---|
| 2,364,391 | 12/1944 | Schiller | 260/429 R X |
| 2,434,402 | 1/1948 | Fleer | 260/429 R X |
| 2,466,925 | 4/1949 | Brauner | 260/429 R |
| 2,608,463 | 8/1952 | Dean | 260/429 R |
| 2,772,260 | 11/1956 | Yeager | 260/429 R X |
| 3,443,916 | 5/1969 | Rolfe | 260/414 X |

*Primary Examiner*—Helen M. S. Sneed
*Attorney, Agent, or Firm*—Robert A. Gerlach

[57] ABSTRACT

The present invention relates to new organosoluble manganese compounds.

According to the invention these compounds are complex organometallic salts of organic or organometalloidic acids in which the ratio R of the number of acid equivalents to the number of manganese atoms is lower than 2. These are produced by reacting at moderately high temperatures in organic or aqueous/organic medium the organic acid with a manganous ammine complex, prepared in situ in the organic reaction medium.

The compounds according to the invention are useful both as drying agents for paints and varnishes as well as combustion additives to liquid fuels.

7 Claims, No Drawings

ORGANOSOLUBLE SALTS OF MANGANESE, PROCESS OF PREPARATION OF SAME

BACKGROUND OF THE INVENTION

The present invention relates to organosoluble salts of manganese, to a process of preparting same, also to organic compounds, liquid fuels, paints and varnishes which contain said organosoluble salts of manganese.

Organosoluble manganese salts are used as oxidation catalysts in chemical operations and especially as combustion additives for liquid fuels of heat generating devices such as fuel oil burners, Diesel motors or propulsion engines, etc., and as drying additives in the paint and varnish industry.

According to prior art, the organosoluble manganese compounds are prepared by reacting a chelating agent in organic medium, such as aminated, borated, B-diketonic, cyclopentadienic derivatives, with a water-soluble manganese salt.

Another known process consists of reacting an alkaline salt of an organosoluble acid with a water-soluble manganese salt.

These reactions are substantially stoichiometric, i.e. the composition of the obtained compounds is such wherein one divalent manganese atom is essentially bound to two organic chains.

The so obtained organosoluble manganese compounds are rather expensive, especially the ones obtained from the B-diketonic and cyclopentadienic derivatives.

Moreover, a relatively large number of organic molecules in relation to the number of manganese atoms is needed for the processes according to prior art as indicated above, in order to obtain an organosoluble manganese compound that can be used as oxidation catalyst in the various chemical operations.

The aim of the present invention is to remedy these drawbacks by providing a solution resulting in low cost especially effective organosoluble manganese salts, having relatively low number of organic molecules compared to the number of manganese atoms.

Preferably, this solution also produces organosoluble manganese salts which are really soluble in organic solvents and oils, solubility attested by the absence of the Tyndall effect in the organic solutions of the foregoing salts.

According to the present invention this solution consists of organosoluble manganese salts which consist of complex organometallic salts of organic and organometalloidic acids, where the ratio R of the number of acid equivalents to the number of manganese atoms is lower than 2. In the present context the term of "number of acid equivalents" denotes the number of organic acid molecules when the acid employed is monofunctional, while this "number of acid equivalents" should be doubled or tripled in the case of the di and tri-acids, and more generally it should be multiplied by the number of acid functions in the case of polyacids.

Preferably, the ratio R should be between 0.2 and 2.

According to a characteristic feature of the present invention, the organic or organometalloidic acids having at least one acid function, i.e. mono, di or poly-acid, is selected from among the organic or organometalloidic acids having from 8 to 30 carbon atoms and preferably from 8 to 25 carbon atoms.

It is advantageous for this organic or organometalloidic acids to have at least one carboxylic or sulphonic or sulphuric or phosphoric acid function and to preferably pertain to the following series:

aliphatic, saturated or unsaturated, straight or branched, cyclic, may be alkyl-substituted, for example the naphthenic acids, aromatic, if necessary substituted by an alkyl radical, especially the carboxylic alkyl-aryl acids, the sulphonic alkyl-aryl acids and the phosphoric alkyl-aryl acids, terpenic, for example the resin acids.

Another aim of the present invention is to provide organic compounds, liquid fuels, paints or varnishes, which contain at least one organosoluble manganese salt according to the present invention.

The concentration of manganese in the organic compounds is relatively high and may reach 400 g of manganese per liter of said organic compounds. Nevertheless, these compounds retain a high degree of fluidity, since their viscosity ranges between 7 and 450 centistokes.

Moreover, said organic compounds indicate a very high degree of stability, since concentrated organic solutions of said organosoluble manganese salts never produce any precipitation of manganese oxide that would be equal to or greater than 0.5% of manganese in solution, even after one year of storage.

Another aim of the present invention is to provide a process of producing such organosoluble manganese salts, according to the present invention, by a method according to which a complex manganous ammine and an organic or organometalloidic acid of the foregoing kind are reacted in aqueous organic medium, by using a ratio R, i.e. the number of acid equivalents in relation to the number of manganese atoms is less than 2, and preferably between 0.2 and 2.

In the present context the term "complex manganous ammine" denotes a divalent manganese complex that comprises ammonia or ammine molecules.

The manganous ammine complex is conveniently prepared, in situ, by reacting in aqueous/organic medium which contains the foregoing organic acid, of an excess amounts of nitrogenated component such as for example ammonia, diethylamine or methylamine, with a water-soluble manganese salt. The water-soluble manganese salt should preferably be a manganous salt such as, for example, manganous sulphate, chloride, acetate, carbonate or nitrate.

The reaction is carried out at moderately elevated temperature, for example between 40° and 60° C., under agitation. At the end of the reaction, to promote separation of residual water originating mainly from the ammonia, and eventually of the water of crystallisation of the water-soluble manganese salt, from the organic phase, the temperature of the reaction medium is increased by 20° to 50° C. in comparison with the initial temperature of the reaction, so that said temperature at the end of the raction should preferably be between 80° and 90° C.

Furthermore, in order to obtain concentrated solutions of manganese, it is advantageous to add the water-soluble manganese salt and the nitrogenated compound in several successive steps into the organic phase. Also, the concentration of manganese in the organic solutions may be controlled by adjusting the proportion of solvent in the organic phase.

The organic phase is separated from water and solid particles by decantation and centrifuging.

The solutions obtained in this manner after separation may be added as they are, following adjustment of concentration, to liquid fuels, paints and varnishes as mentioned earlier, to serve, as required, as combustion additive or drying compound.

Various other objects and advantages and characteristic features of the present invention will be observed from the following description, with reference to several examples in the form thereof presented, while it is not desired to be limited thereto.

EXAMPLE 1

260 g of technical grade oleic acid (acid number=193) are dissolved in 750 cm$^3$ white spirit and, under good agitation 870 g of manganese acetate tetrahydrate are dissolved. Still under agitation 1,200 cm$^3$ of 20° Baume ammonia are added slowly. By the time the addition is finished, the reaction increases the temperature of the medium to approx. 45° C. Then for 5 hours the mixture is maintained at 55° C. under more energetic agitation. Then the mixture is brought to 85° C. to ensure decantation of water. After allowing the solution to stand, the residual water is eliminated by decantation.

The supernatant organic phase is centrifuged in order to eliminate small quantities of oxide and water remaining in suspension. In this way a dark-brown coloured organic solution of a complex manganese salt is obtained. The ratio R, which represents the number of oleic acid molecules in proportion to the number of manganese atoms, is equal to 0.26. This ratio R is calculated by determining the content of manganese in the organic phase.

This organic solution is very fluid (viscosity at 20° C.=8.5 cst) and its concentration is equal to 155 g/l of manganese.

After 6 months in storage, the concentration of manganese in the solution did not vary appreciably.

EXAMPLE 2

Under energetic agitation 800 g of fatty acid obtained from paper-making residue (fatty acid of "tall oil") are poured into 600 cm$^3$ of white spirit, and acid number of fatty acid being 182. Under agitation 200 g of manganese sulphate monohydrate are dispersed in the solution to which 400 ml of 20° Baume ammonia are slowly added. This latter operation is repeated two more times. The reaction time between each such addition of manganese sulphate and ammonia is 2 hours, the temperature of the reaction medium being maintained between 50° and 55° C. At the end of the third addition stirring is continued for another hour and the temperature is progressively increased to 85° C. to ensure decantation of water in the bottom phase. Following separation of water the obtained organic phase contains 128 g of manganese per liter.

Following the same operating procedure 100 g of manganese sulphate and 1,200 cm$^3$ ammonia are added to the organic phase. The manganese concentration in the new organic solution thus obtained is 252 g per liter.

After a third recharging with manganese sulphate and ammonia, carried out in a manner analogous to the second recharging, at that time the aqueous phase is on top. The organic phase is centrifuged to eliminate the water and the residual oxides.

The complex manganese salt contained in the organic phase has a ratio R of number of fatty acid molecules to manganese molecules equal to 0.23.

The organic solution is soluble in aliphatic solvents and its viscosity is 330 cst at 20° C.

The example illustrates that by three successive charges of water-soluble manganese salt and ammonia an organic solution of very high manganese concentration (375 g/l manganese) is obtained.

EXAMPLE 3

The procedure described in Example 1 is followed, with addition of 330 g of linoleic acid (acid number 195) dissolved in 200 cm$^3$ of white spirit, 205 g of manganous carbonate and 280 cm$^3$ of ammonia.

The brown organic solution thus obtained contains 148 g/l of manganese.

The ratio R of the organosoluble manganese salt in this solution is equal to 0.66.

EXAMPLE 4

The operating procedure described in Example 2 is followed, by reacting 460 g of pure dodecybenzene sulphonic acid in 500 cm$^3$ of white spirit with 740 g of anhydrous manganous chloride and 1,100 cm$^3$ or 20° Baume ammonia.

This operation is carried out with two rechargings.

An organic solution of a complex manganese salt is obtained wherein the ratio R of the number of organic acid molecules to the number of manganese atoms is equal to 0.24. The quantity of this complex salt contained in said solution corresponds to 245 g of manganese per liter.

EXAMPLE 5

The procedure of Example 2 is followed by reacting 430 g of dinonylphenoxy phosphoric acid (acid number 240), dissolved in 250 cm$^3$ of white spirit, with 398 g of manganous nitrate hexahydrate and with 1,350 cm$^3$ of ammonia.

The operation is carried out in two successive steps of recharging.

The brown solution thus obtained contains 102 g of manganese per liter.

The ratio R of the complex manganese salt contained in the solution, representing the ratio between the number of acid molecules and manganese atoms, is equal to 0.73.

While the invention has been described in great detail and with respect to the present preferred forms thereof, it is not to be considered exhaustive thereto since many changes and modifications may be made therein without departing from the spirit and scope of the invention as defined in the following claims.

We claim:

1. An organosoluble salt of manganese useful as a combustion additive to liquid fuels and as a drying additive for liquid paints and varnishes, consisting of a complex organometallic salt being the reaction product of an organic or organometalloidic acid having at least one acid function and having from 8 to 30 carbon atoms in each molecule, said acid being selected from the group consisting of oleic acid, linoleic acid, fatty acids of tall oil, resin acids, dodecylbenzene sulfonic acid, dinonylphenoxy phosphoric acid and napthenic acids, reacted with a complex manganous ammine wherein the ammine is derived from ammonia and the ratio of the number of acid equivalents to the number of manganese atoms is between 0.2 and 2.0.

2. A process of producing an organosoluble salt of manganese comprising the steps of:

(a) providing an aqueous/organic medium;
(b) dissolving in said medium an organic or an organometallodic acid having at least one acid function and from 8 to 30 carbon atoms in each molecule and selected from the group consisting of oleic acid, linoliec acid, fatty acids of tall oil, resin acids, dodecylbenzene sulfonic acid, dinonylphenoxy phosphoric acid and naphthenic acids; and
(c) reacting a manganous ammine complex with said acid in an amount sufficient to provide a ratio of acid equivalents to manganese atoms of between 0.2 and 2.0, said manganous ammine complex being obtained by reacting in said aqueous organic medium, an excess amount of an ammine selected from the group consisting of diethylamine, methylamine and ammonia with a water soluble manganous salt.

3. The process of claim 2 wherein said water-soluble manganese salt is selected from the group consisting of manganous sulphate, manganous chloride, manganous acetate, manganous carbonate and manganous nitrate.

4. The process of claim 2 wherein said water-soluble manganese salt and said ammine are added in several successive steps into the aqueous organic medium in which the organic or organometallic acid had been dissolved.

5. The process of claim 2 wherein the aqueous/organic medium includes
an organic solvent to solubilise said organic or organometallodic acid, and
residual water originating from said ammine,
and that during the reaction said aqueous/organic medium is maintained at a temperature of between 40° and 60° C.

6. The process of claim 5 including the step of raising the temperature of said aqueous/organic medium by 20° to 50° C. at the end of the reaction in comparison with the initial temperature, so that said temperature at the end of the reaction is between 80° and 90° C., whereby separation of water from the aqueous/organic medium is facilitated.

7. The process of claim 2 wherein said ammine is ammonia.

* * * * *